(12) United States Patent
Scheib et al.

(10) Patent No.: US 9,913,655 B2
(45) Date of Patent: Mar. 13, 2018

(54) SURGICAL INSTRUMENT WITH ACTIVE ELEMENT AND SUCTION CAGE

(71) Applicant: Ethicon Endo-Surgery, Inc., Cincinnati, OH (US)

(72) Inventors: Charles J. Scheib, Loveland, OH (US); Edward G. Chekan, Cincinnati, OH (US); Chad P. Boudreaux, Cincinnati, OH (US); Frederick E. Shelton, IV, Hillsboro, OH (US); Tamara S. Vetro Widenhouse, Clarksville, OH (US)

(73) Assignee: Ethicon LLC, Guaynabo, PR (US)

( * ) Notice: Subject to any disclaimer, the term of this patent is extended or adjusted under 35 U.S.C. 154(b) by 168 days.

(21) Appl. No.: 14/082,287

(22) Filed: Nov. 18, 2013

(65) Prior Publication Data
US 2015/0142032 A1   May 21, 2015

(51) Int. Cl.
*A61B 17/32* (2006.01)
*A61B 17/22* (2006.01)

(52) U.S. Cl.
CPC ............ *A61B 17/320068* (2013.01); *A61B 17/22004* (2013.01); *A61B 2017/32008* (2013.01);
(Continued)

(58) Field of Classification Search
CPC ............ A61B 17/29; A61B 17/221; A61B 17/320068; A61B 2017/320072; A61B 2017/32008; A61B 17/22004; A61B 17/22012; A61B 2017/2901; A61B 2017/306; A61B 2017/308; A61B 2217/005; A61B 2017/320076; A61B 2017/22031; A61B 2017/22034; A61B 2017/22035; A61B 2017/22079; A61B 1/015; A61B 17/28; A61B 17/2804; A61B 17/2812; A61B 17/2816; A61B 17/282; A61B 17/2833; A61B 17/3201; A61B 17/320092; A61B 2017/28; A61B 2017/2804; A61B 2017/2812;
(Continued)

(56) References Cited

U.S. PATENT DOCUMENTS 5,322,055 A    6/1994  Davison et al.
5,417,709 A *  5/1995  Slater ............ A61B 17/320016
                                                 604/27
(Continued)

FOREIGN PATENT DOCUMENTS

EP        1090658    * 11/2001

OTHER PUBLICATIONS

U.S. Appl. No. 13/657,553, filed Oct. 22, 2012.
(Continued)

*Primary Examiner* — Katrina Stransky
*Assistant Examiner* — Kankindi Rwego
(74) *Attorney, Agent, or Firm* — Frost Brown Todd LLC

(57) ABSTRACT

A surgical system comprises an end effector for operating on tissue and a screen positioned around the end effector. The screen is fluidly coupled with a suction source by a conduit such as a tube. The screen is configured to communicate suction through the screen while preventing tissue from contacting the end effector. The screen is further configured to retract proximally relative to the end effector to thereby expose the end effector.

20 Claims, 6 Drawing Sheets

(52) U.S. Cl.
CPC ............. *A61B 2017/320044* (2013.01); *A61B 2017/320072* (2013.01); *A61B 2017/320076* (2013.01)

(58) Field of Classification Search
CPC ...... A61B 2017/2816; A61B 2017/282; A61B 2017/2833; A61B 10/02; A61B 10/0233; A61B 10/0241; A61B 10/025; A61B 10/02566; A61B 10/0275; A61B 10/0283; A61B 10/0291; A61B 10/04; A61B 10/06; A61B 2010/0208; A61B 2010/0216; A61B 2010/0225; A61B 2010/0258; A61B 2010/045; A61B 2017/2926; A61B 2017/2927; A61B 2017/2929; A61B 2017/2931; A61B 2017/2932; A61B 2017/2933; A61B 2017/2934; A61B 2017/2936; A61B 2017/2937; A61B 2017/2938; A61B 2017/2939; A61B 2017/294; A61B 2017/2941; A61B 2017/2943; A61B 2017/2944; A61B 2017/2945; A61B 2017/2946; A61B 2017/2947; A61B 2017/2948; A61B 2017/295; A61B 2017/320084; A61B 2017/320088; A61B 2017/320096; A61F 9/00745
USPC .................................................. 606/205, 207
See application file for complete search history.

(56) References Cited

U.S. PATENT DOCUMENTS

| | | | |
|---|---|---|---|
| 5,505,710 A * | 4/1996 | Dorsey, III | A61M 1/008 604/158 |
| 5,873,873 A | 2/1999 | Smith et al. | |
| 5,980,510 A | 11/1999 | Tsonton et al. | |
| 6,080,175 A * | 6/2000 | Hogendijk | A61B 17/320016 606/167 |
| 6,110,127 A * | 8/2000 | Suzuki | A61B 10/06 600/564 |
| 6,325,811 B1 | 12/2001 | Messerly | |
| 6,682,543 B2 * | 1/2004 | Barbut et al. | 606/159 |
| 6,773,444 B2 | 8/2004 | Messerly | |
| 6,783,524 B2 | 8/2004 | Anderson et al. | |
| 6,846,314 B2 | 1/2005 | Shapira | |
| 8,461,744 B2 | 6/2013 | Wiener et al. | |
| 8,591,536 B2 | 11/2013 | Robertson | |
| 8,623,027 B2 | 1/2014 | Price et al. | |
| 8,721,529 B2 | 5/2014 | Hess et al. | |
| 9,393,037 B2 | 7/2016 | Olson et al. | |
| 2006/0079874 A1 | 4/2006 | Faller et al. | |
| 2006/0229659 A1 * | 10/2006 | Gifford | A61B 17/2202 606/200 |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0125040 A1 * | 5/2009 | Hambly | A61B 17/30 606/148 |
| 2010/0069940 A1 | 3/2010 | Miller et al. | |
| 2011/0087212 A1 | 4/2011 | Aldridge et al. | |
| 2012/0112687 A1 | 5/2012 | Houser et al. | |
| 2012/0116265 A1 | 5/2012 | Houser et al. | |

OTHER PUBLICATIONS

U.S. Appl. No. 61/410,603, filed Nov. 5, 2010.

International Search Report and Written Opinion dated Jan. 28, 2015 for Application No. PCT/US2014/065407, 10 pgs.

* cited by examiner

SURGICAL INSTRUMENT WITH ACTIVE ELEMENT AND SUCTION CAGE

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, and issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, and issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, and issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," published as U.S. Pat. Pub. No. 2014/0114334 on Apr. 24, 2014, and issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
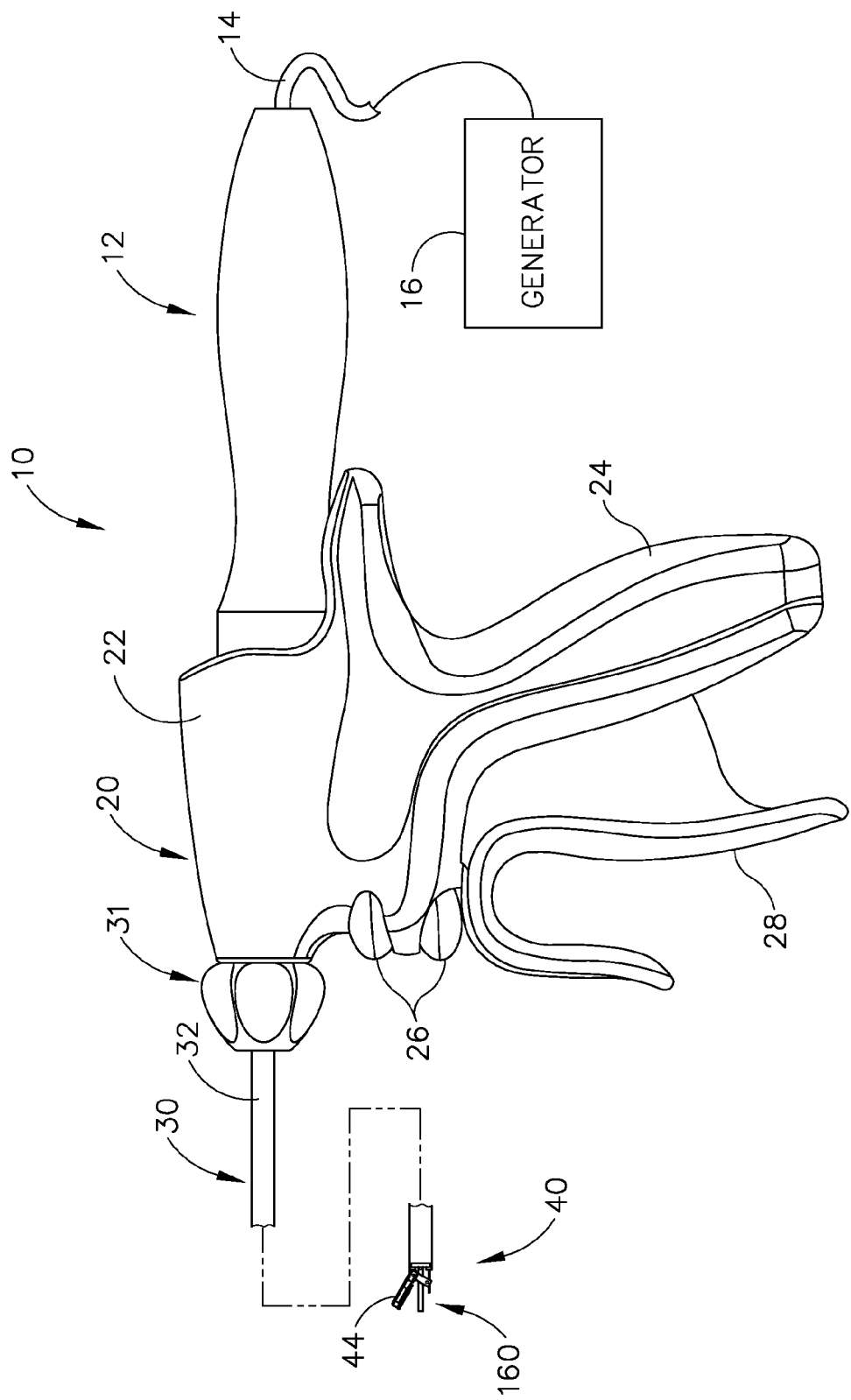
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750 (now U.S. Pat. No. 8,623,027); U.S. Pub. No. 2010/0069940, now U.S. Pat. No. 9,023,071; U.S. Pub. No. 2011/0015660, now U.S. Pat. No. 8,461,744, issued Jun. 11, 2013; U.S. Pub. No. 2012/0112687, now U.S. Pat. No. 9,381,058; U.S. Pub. No. 2012/0116265; U.S. patent application Ser. No. 13/538,588, now U.S. Pat. No. 9,393,037 issued Jul. 19, 2016; U.S. patent application Ser. No. 13/657,553, now U.S. Pat. No. 9,095,367, issued Aug. 4, 2015; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

End effector (40) of the present example comprises clamp arm (44) and ultrasonic blade (160). Clamp arm (44) includes a clamp pad (not shown) that is secured to the underside of clamp arm (44), facing blade (160). Clamp arm

(44) is operable to selectively pivot toward and away from blade (160) to selectively clamp tissue between clamp arm (44) and blade (160) in response to pivoting of trigger (28) toward pistol grip (24). Blade (160) of the present example is operable to vibrate at ultrasonic frequencies in order to effectively cut through and seal tissue, particularly when the tissue is being clamped between clamp arm (44) and blade (160). Blade (160) is positioned at the distal end of an acoustic drivetrain that includes transducer assembly (12) to vibrate blade (160). By way of example only, the acoustic drivetrain may be configured in accordance with various teachings of various references that are cited herein.

In the present example, the distal end of blade (160) is located at a position corresponding to an anti-node associated with resonant ultrasonic vibrations communicated through a flexible acoustic waveguide, in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (44), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

II. Exemplary Ultrasonic Surgical Instrument With Suction

In some instances, it may be desirable to provide suction at a target location to evacuate excess fluid and improve visibility. Accordingly, a mesh screen may be used to selectively cover end effector (40) such that suction may be applied through the screen to the target location. The screen may allow a user to apply suction without having to introduce a separate suctioning instrument; and may further prevent the user from inadvertently grabbing tissue with end effector (40) while suction is being applied. The screen may also be used to passively separate tissue planes with or without applying suction. The example below includes several merely illustrative versions of a surgical instrument with a screen that may be readily introduced to an instrument (10). It should be understood that a screen is just one merely illustrative example of a structure that may be used as a blocking element to selectively cover end effector (40). Other suitable structures that may be used as a blocking element to selectively cover end effector (40) will be apparent to those of ordinary skill in the art in view of the teachings herein.

A. Exemplary Screen

Figure 2:
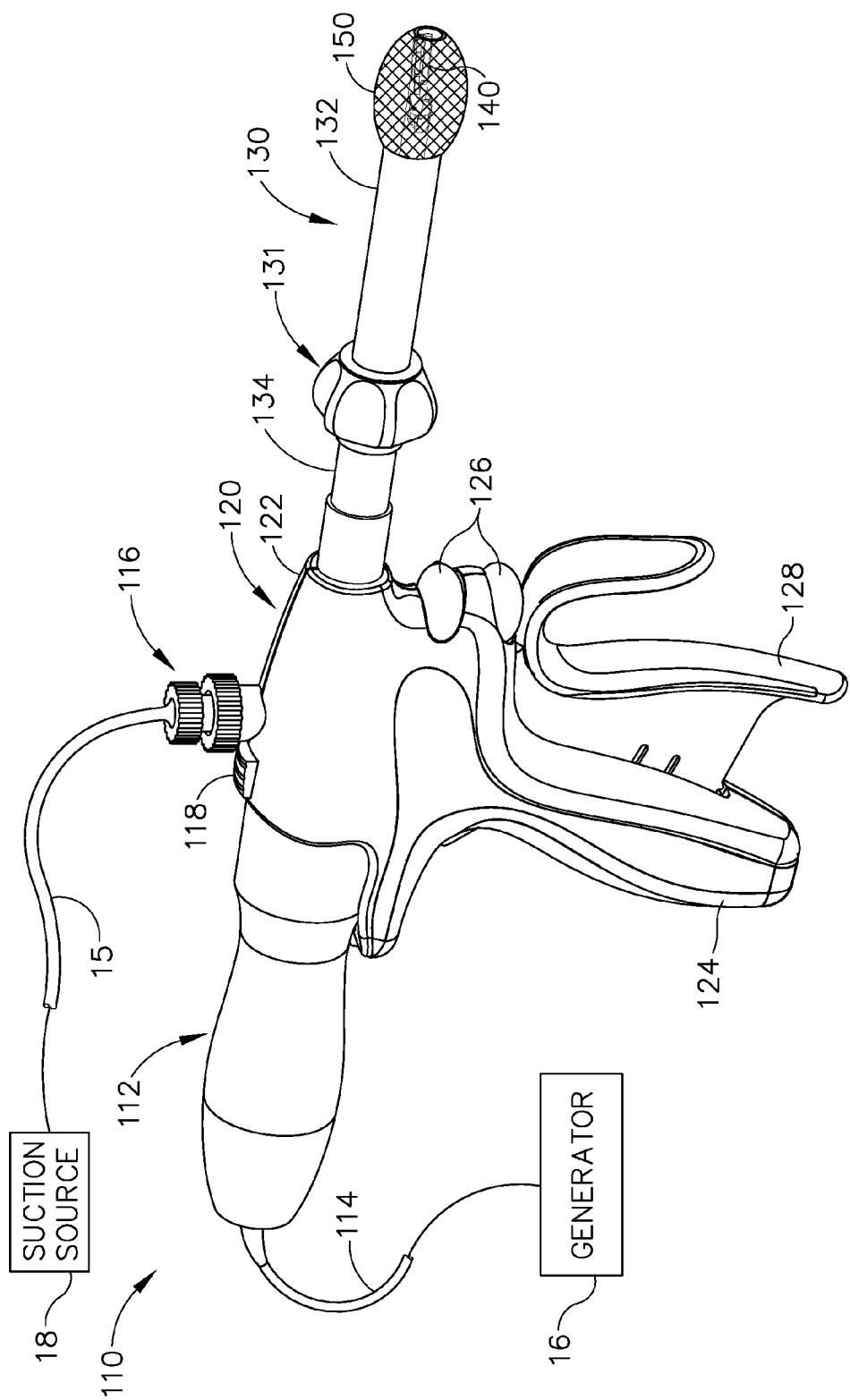
FIG. 2 depicts a side elevational view of another exemplary ultrasonic surgical instrument.

FIG. 2 shows an exemplary ultrasonic surgical instrument (110) with suction capabilities. Instrument (110) is similar to instrument (10) in that instrument (110) comprises an end effector (140), a shaft assembly (130), a transducer assembly (112), and a handle assembly (120). End effector (140) is similar to end effector (40), except that a screen (150) is selectively positioned over end effector (140). Screen (150) comprises a mesh configuration that allows suction to be applied through screen (150) at end effector (140) by suction source (18), while preventing tissue from entering through screen (150) to end effector (140). Accordingly, suction may be applied by instrument (110) without inadvertently grabbing tissue with end effector (140). It should be understood that the suction may flow in various directions relative to screen (150) including but not limited to paths extending radially inwardly toward end effector (140) through the sidewall defined by screen (150). In other words, the suction provided through screen is not necessarily limited to suction along a path that is oriented along the longitudinal axis of shaft assembly (130).

Screen (150) further allows a user to perform blunt tissue dissection such that screen (150) is used to drive apart tissue layers without actively cutting the tissue with end effector (140). Although screen (150) of the present example comprises a mesh configuration, other suitable screen (150) configurations will be apparent to one with ordinary skill in the art in view of the teachings herein.

Screen (150) is retractable relative to end effector (140) such that end effector (140) may be selectively exposed to perform active tissue cutting and/or coagulation as described above. The combination of suction, passive and/or active tissue separation by instrument (110) could enable a user to be more efficient and allow for one handed control of suction. As shown in FIG. 2, screen (150) is coupled to the distal end of shaft assembly (130). Shaft assembly (130) is similar to shaft assembly (30) of instrument (10), except that shaft assembly (130) comprises outer shafts (132, 134) that allow for the retraction of screen (150) relative to end effector (140). Outer shafts (132, 134) are positioned to encompass shaft (32) that couples end effector (140) with handle assembly (120). Outer shaft (132) couples screen (150) to rotation knob (131) and outer shaft (134) couples rotation knob (131) to handle portion (120). Outer shaft (134) is retractable relative to handle portion (120). Accordingly, the user may retract outer sheath (134) to thereby retract rotation knob (131), outer sheath (132), and screen (150) to expose end effector (140). Outer sheath (134) may be manually retracted by grasping rotation knob (131), or coupled with trigger (128) of handle assembly (120) such that outer sheath (134) is retracted when trigger (128) is pivoted toward grip (124) of handle assembly (120). Outer shaft (134) has a sufficient length that allows screen (150) to be retracted to fully expose end effector (140) before rotation knob (131) contacts handle assembly (120). While the present example describes retracting screen (150) relative to end effector (140), end effector (140) may be configured to extend distally relative to screen (150). Other suitable configurations to selectively expose end effector (140) from screen (150) will be apparent to one of ordinary skill in the art in view of the teachings herein.

Figure 3:
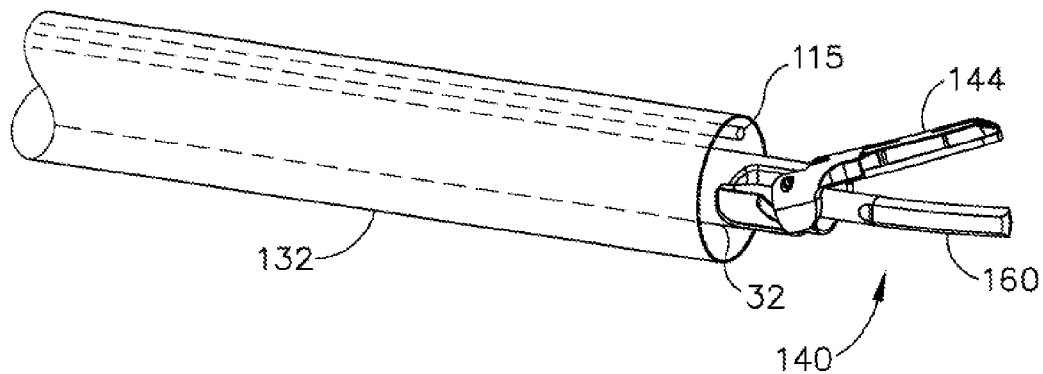
FIG. 3 depicts a partial perspective view of an end effector of the surgical instrument of FIG. 2 with a shield removed.

Shaft assembly (130) further comprises a suction tube (115) to fluidly communicate suction from suction source (18) to screen (150). FIG. 3 shows the distal portion of instrument (110) with screen (150) removed. Suction tube (115) extends through shaft assembly (130) between shaft (32) and outer shafts (132, 134) such that the distal end of suction tube (115) is positioned proximal to end effector (140). With the distal end of suction tube (115) positioned proximal to end effector (140), suction tube (115) may or may not be retracted with screen (150). Of course, the distal end of suction tube (115) may extend further within screen (150) and may be retracted with screen (150). Other suitable configurations for suction tube (115) will be apparent to one with ordinary skill in the art in view of the teachings herein.

Figure 4:
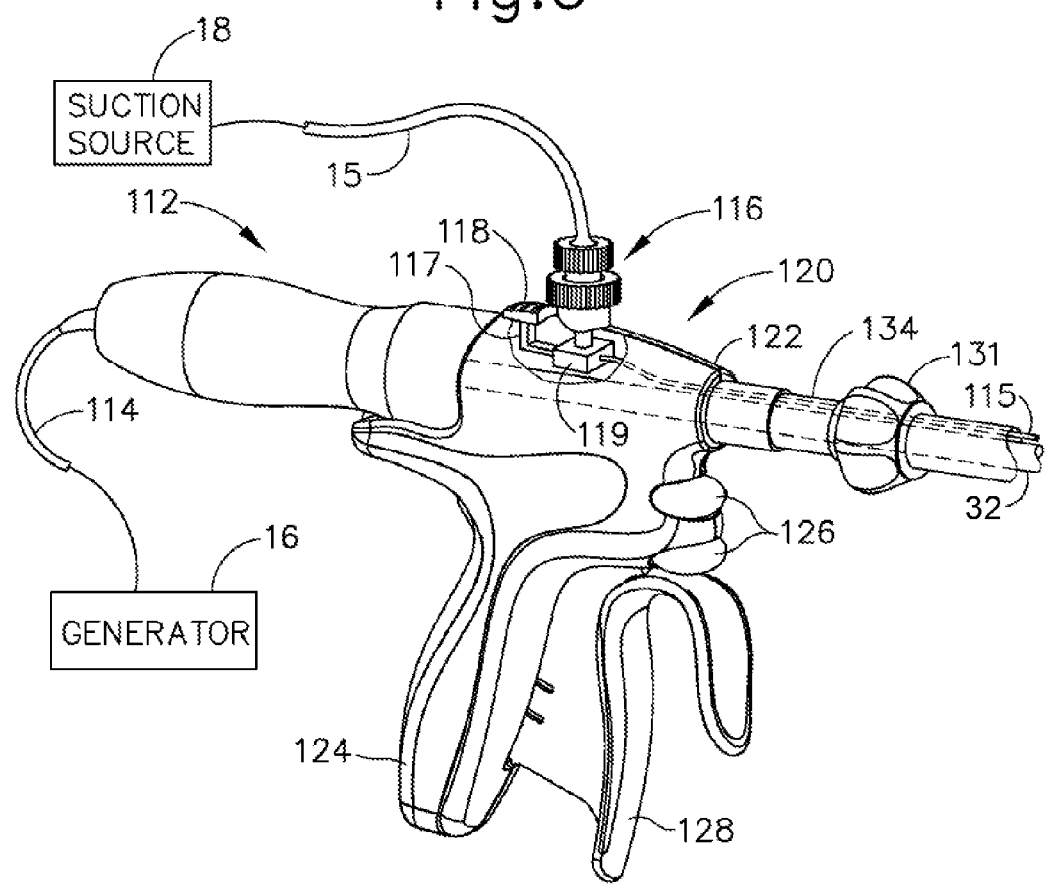
FIG. 4 depicts a side elevational view of a handle assembly of the surgical instrument of FIG. 2.

Handle assembly (120) is similar to handle assembly (20) in that handle assembly (120) comprises a body (122) including a pistol grip (124), a pair of buttons (126), and a trigger (128) that is pivotable toward and away from pistol grip (124). Transducer assembly (112) is coupled with a generator (16) via a cable (114). Suction tube (115) extends through handle assembly (120) to a connector (116), as shown in FIG. 4. Connector (116) then couples suction source (18) to handle assembly (120) via tube (15). Accordingly, suction source (18) is in fluid communication with screen (150) through tube (15), connector (116), and suction tube (115). Connector (116) is fluid tight, yet is selectively removable from handle assembly (120) such that suction source (18) is selectively coupled with handle assembly (120). Handle assembly (120) further comprises a suction actuator (118) and a valve (119) that allows suction to be selectively applied to instrument (110). FIG. 4 shows valve (119) positioned around suction tube (115) such that valve (119) is opened and/or closed to open and/or close suction tube (115). When valve (119) is open, suction tube (115) is open to allow suction to pass through suction tube (115). When valve (119) is closed, valve (119) closes suction tube (115) to prevent suction from passing through suction tube (115). In the present example, suction actuator (118) comprises a button used to actuate valve (119). Suction actuator (118) is electrically coupled to valve (119) by wires (117). In this configuration, valve (119) may include a solenoid. In other versions, suction actuator (118) is mechanically coupled with valve (119) to open and/or close valve (119). Accordingly, a user may actuate suction actuator (118) to selectively apply suction at screen (150) when screen (150) is positioned over end effector (140). Of course, suction actuator (118) is merely optional.

In some versions, screen (150) is covered with another material. Such an additional material may be removable or non-removable from screen (150). By way of example only, such a material may be cloth like, such as a gauze material. Such an additional cloth material may provide absorption of blood and/or other bodily fluid, such that the operator may use the cloth material to dab up pools of blood and/or other bodily fluid. In addition or in the alternative, such an additional cloth material may provide further gripping during blunt dissection. The additional cloth material may stretch over screen (150) and/or be permanently adhered to screen (150). As another merely illustrative example, screen (150) may be coated with a textured material, such as a sprayed-on absorbent plastic material, etc. Other suitable features that may be added to or incorporated into screen (150) will be apparent to those of ordinary skill in the art in view of the teachings herein.

B. Exemplary Operation

Figure 5A:
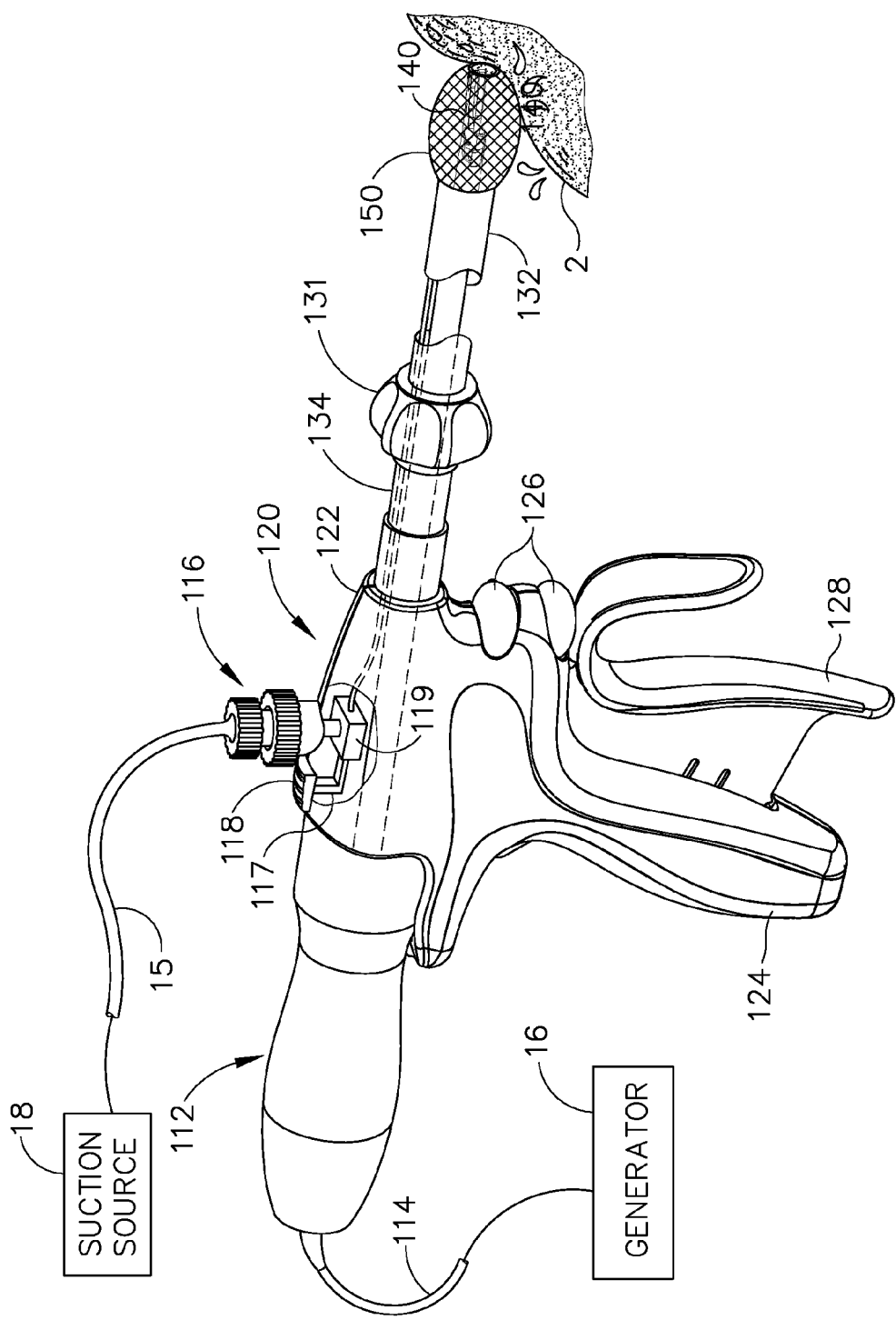
FIG. 5A depicts a side elevational view of the surgical instrument of FIG. 2, showing suction being applied to tissue.
Figure 5B:
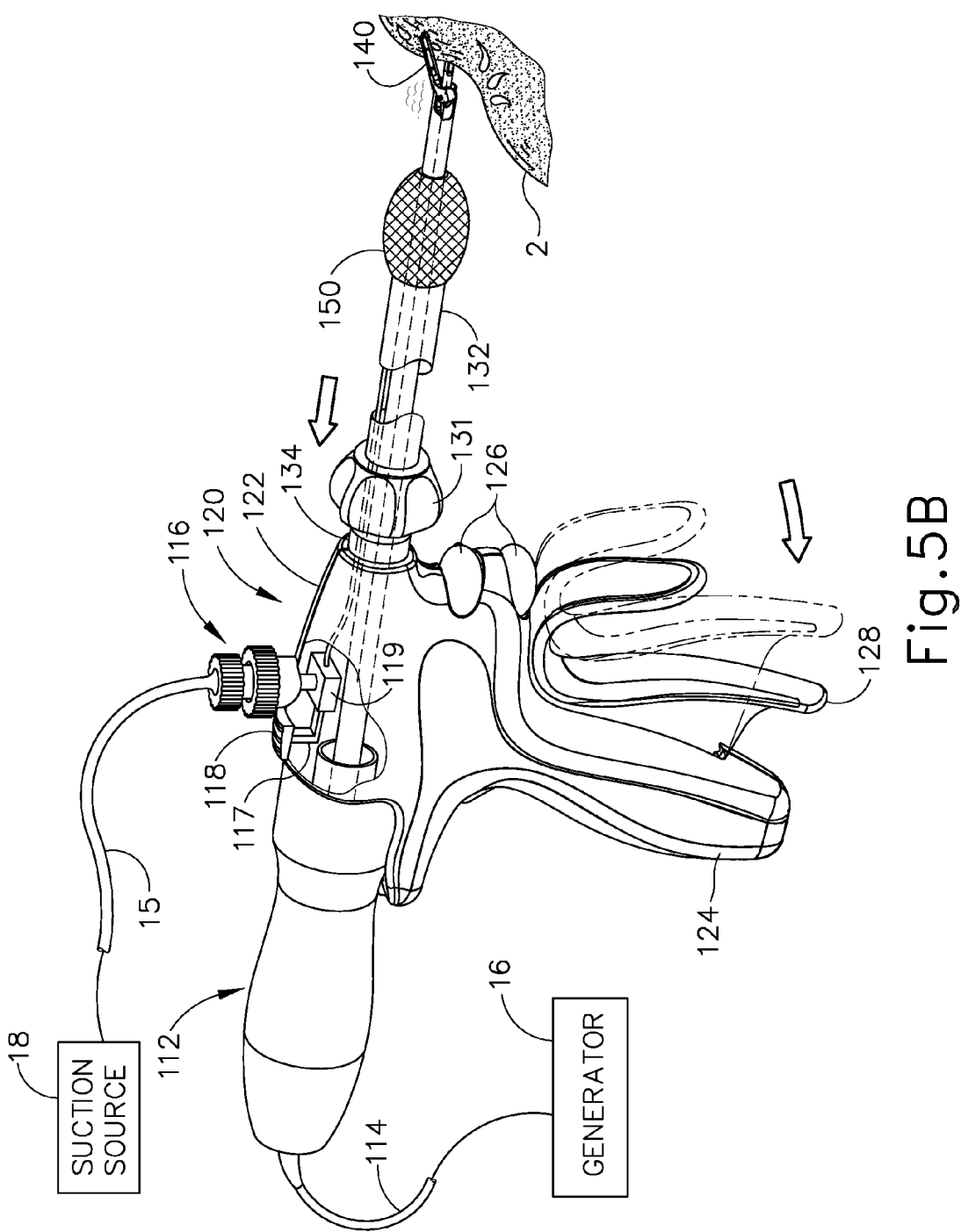
FIG. 5B depicts a side elevational view of the surgical instrument of FIG. 2, showing the end effector being applied to tissue.
Figure 6:
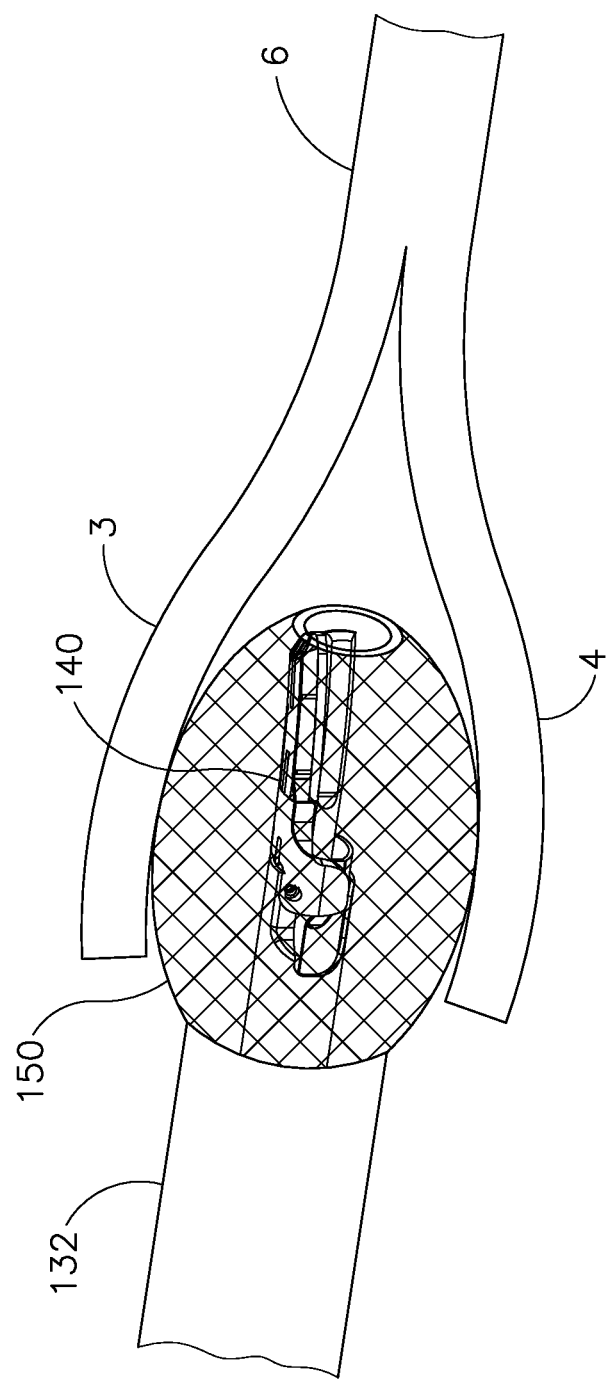
FIG. 6 depicts a a partial side elevational view of the screen of the surgical instrument of FIG. 2 dissecting tissue.

FIGS. 5A-6 show an exemplary operation of instrument (110). Instrument (110) is inserted into a patient with screen (150) extended distally to cover end effector (140), as shown in FIG. 5A. With screen (150) in the extended position, instrument (110) may be used to provide suction to a desired location. In the present example, screen (150) is pressed against tissue (2) remove blood and/or other fluid from tissue (2). Suction actuator (118) is then actuated to open valve (119) and suction tube (115). This communicates suction from suction source (18) to screen (150) through suction tube (115). Fluids are then drawn from tissue (2) through screen (150) and suction tube (115). While suction is applied, screen (150) prevents tissue (2) from entering through screen (150) to reach end effector (140). Once the desired amount of fluid is removed from the site, suction actuator (118) is again actuated to close valve (119) and suction tube (115) to prevent suction from applied from suction source (18) to screen (150). Of course, suction actuator (118) may be actuated again to apply additional suction to tissue (20), or suction actuator (118) may be actuated at another desired location.

Surgical instrument (110) is further used to provide active tissue dissection and/or separation to tissue (2), as shown in FIG. 5B. In the present example, rotation knob (131) is grasped and slid proximally relative to handle assembly (120) to thereby retract outer shafts (132, 134) and screen (150). In some versions, trigger (128) of handle assembly (120) is pivoted toward grip (124) to retract outer shafts (132, 134) and screen (150) proximally. Screen (150) is thereby retracted to expose end effector (140). Trigger (128) is then squeezed toward grip (124) to pivot clamp arm (144) relative to ultrasonic blade (160) to capture tissue (2) between clamp arm (144) and blade (160). It should be noted that clamp arm (144) is merely optional and could be omitted if desired. A selected one of buttons (126) may then be pressed to activate transducer assembly (112) to actively cut and/or coagulate tissue (20). Rotation knob (131) may then be slid distally relative to handle assembly (120) to advance outer shafts (132, 134) and screen (150) distally to recover end effector (140), as shown in FIG. 5A. In some versions, rotation knob (131) is resiliently biased in the distal direction such that rotation knob (131) translates distally when rotation knob (131) is released by the user.

In some versions, suction source (18) is operable to provide a dual suction mode. In a first suction mode, suction source (18) may apply a high amount of suction to screen (150) to allow screen (150) to grab tissue (2). In a second suction mode, suction source (18) may apply a lower amount of suction to screen (150) such that suction is applied through screen (150) to draw fluids through screen (150) without grabbing tissue (2).

In some versions, screen (150) is expandable to allow screen (150) to be inserted through a trocar. For example, screen (150) is in a collapsed configuration when screen (150) is inserted through the trocar and then selectively expanded within the patient. Screen (150) may be moved between the collapsed configuration and the expanded configuration by advancing and/or retracting one end of screen (150) relative to the other end of screen (150).

With screen (150) in the extended position, instrument (110) may further be used for blunt tissue dissection. FIG. 6 shows screen (150) being inserted between layers (3, 4) of tissue (6). Screen (150) may be manipulated by the user with handle assembly (120) to dissect tissue layers (3, 4) by driving tissue layers (3, 4) apart. Suction may be applied while screen (150) is dissecting tissue layers (3, 4) or suction may be applied to the newly separated tissue layers (3, 4).

Although instrument (110) has been described as adding suction capabilities to an ultrasonic device, it should be noted that the exemplary suction capabilities could also be applied to monopolar RF electrosurgical devices, bipolar RF electrosurgical devices, and/or other suitable surgical instruments.

III. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system comprising:
   (a) an end effector operable to manipulate tissue, wherein the end effector comprises:
      (i) an ultrasonic blade, and
      (ii) a clamp arm configured to pivot relative to the ultrasonic blade to clamp tissue between the ultrasonic blade and the clamp arm;
   (b) a blocking element positioned around the end effector, wherein the blocking element is movable relative to the end effector;
   (c) a suction source;
   (d) a conduit configured to provide fluid communication between the blocking element and the suction source; and
   (e) an outer tube, wherein the blocking element is positioned on the outer tube, wherein the conduit is positioned within the outer tube;
   wherein the blocking element includes a mesh screen and is configured to communicate suction through the mesh screen to the tissue.

2. The system of claim 1, wherein the blocking element is translatable relative to the end effector.

3. The system of claim 2, wherein the blocking element is retractable to a proximal position to expose the end effector from the blocking element.

4. The system of claim 3 further comprising a trigger, wherein the trigger is operable to retract the blocking element.

5. The system of claim 1 further comprising an outer shaft extending proximally from the blocking element, wherein the outer shaft is configured to house the conduit.

6. The system of claim 1 further comprising a valve coupled to the conduit, wherein the valve is configured to selectively apply suction through the conduit to the blocking element.

7. The system of claim 6 further comprising an actuator, wherein the actuator is configured to selectively actuate the valve.

8. The system of claim 6, wherein the valve is configured to apply suction to the blocking element when the blocking element is in an extended position such that blocking element is covering the end effector.

9. The system of claim 6, wherein the valve is configured to not apply suction to the blocking element when the blocking element is in a retracted position such that the blocking element is exposing the end effector.

10. The system of claim 1 further comprising an ultrasonic transducer assembly coupled with the end effector.

11. The system of claim 1, wherein the blocking element is operable to perform a blunt dissection of tissue.

12. The system of claim 1 further comprising a body and a shaft coupling the blocking element to the body.

13. The system of claim 12, wherein the shaft is translatable relative to the body.

14. The system of claim 1, wherein the blocking element is configured to prevent the tissue from entering through the blocking element to engage the end effector.

15. An apparatus comprising:
(a) a shaft;
(b) an end effector coupled to the shaft, wherein the end effector includes a pivoting clamp arm configured to pivot relative to the shaft for clamping tissue at a distal end portion of the end effector;
(c) an actuator;
(d) a screen, wherein the screen is axially retractable relative to the end effector from a first position to a second position in response to actuation of the actuator, wherein the screen is configured to house the end effector in the first position, wherein the screen is configured to expose the end effector in the second position; and
(e) a suction source, wherein the screen is in fluid communication with the suction source, wherein the screen is configured to communicate suction through the screen from the suction source when the screen is in the first position, wherein the screen is configured to cease communication of suction from the suction source in response to actuation of the actuator and the screen transitioning from the first position to the second position.

16. An apparatus comprising:
(a) a body;
(b) a shaft assembly, comprising:
   (i) an inner shaft comprising a proximal end and a distal end, wherein the proximal end of the inner shaft is coupled to the body, wherein the inner shaft is longitudinally fixed relative to the body,
   (ii) an outer shaft coupled to the body and having a proximal outer shaft portion and a distal outer shaft portion, and
   (iii) an actuator member arranged between the proximal and distal outer shaft portions,
   wherein a proximal end of the proximal outer shaft portion is slidably received within the body such that the outer shaft is configured to move longitudinally relative to the body and the inner shaft between an extended position and a retracted position in which at least a portion of the proximal outer shaft portion is disposed within the body;
(c) an end effector at the distal end of the inner shaft, wherein the end effector is operable to manipulate tissue; and
(d) a screen coupled to the distal outer shaft portion, wherein the screen is axially retractable relative to the end effector from a first screen position when the outer shaft is in the extended position, to a second screen position in response to proximal movement of the outer shaft to the retracted position, wherein the screen is configured to house the end effector in the first screen position, wherein the screen is configured to expose the end effector in the second screen position;
wherein the screen is in fluid communication with a suction source, wherein the screen is configured to communicate suction through the screen from the suction source when the screen is in the first screen position.

17. The apparatus of claim 1, wherein the conduit is in the form of a tube that extends axially within the outer tube.

18. The apparatus of claim 1, wherein the blocking element is longitudinally retractable relative to the end effector, and the clamp arm is configured to clamp tissue against the ultrasonic blade when the blocking element is in a retracted position.

19. The apparatus of claim 15, wherein the end effector includes a blade and a pivotable clamp arm configured to clamp tissue against the blade.

20. The apparatus of claim 16, wherein the screen comprises a mesh material.

* * * * *